United States Patent [19]

Ruest et al.

[11] Patent Number: 4,524,077

[45] Date of Patent: Jun. 18, 1985

[54] LIQUID 2-HYDROXY-4-METHYLTHIOBUTYRIC ACID AND PROCESS FOR THE PREPARATION THEREOF

[75] Inventors: Dennis A. Ruest, Manchester; Masaharu Takano, St. Louis; Lawrence R. Wolf, Creve Coeur, all of Mo.

[73] Assignee: Monsanto Company, St. Louis, Mo.

[21] Appl. No.: 550,857

[22] Filed: Nov. 14, 1983

[51] Int. Cl.³ .................. A01N 37/02; C07C 149/14
[52] U.S. Cl. .................. 514/557; 562/581; 564/129
[58] Field of Search .............. 562/581; 424/317; 564/129

[56] References Cited

U.S. PATENT DOCUMENTS

| | | | |
|---|---|---|---|
| 2,745,745 | 5/1956 | Blake et al. | 562/581 |
| 2,938,053 | 5/1960 | Blake et al. | 562/581 |
| 3,175,000 | 3/1965 | Gielkens et al. | 562/581 |
| 3,773,927 | 11/1973 | Cummins | 424/166 |
| 4,310,690 | 1/1982 | Cummins | 562/581 |

FOREIGN PATENT DOCUMENTS 915193  1/1963  United Kingdom ............ 562/581

*Primary Examiner*—Natalie Trousof
*Assistant Examiner*—Bruce D. Gray
*Attorney, Agent, or Firm*—William H. Duffey; Dennis R. Hoerner, Jr.

[57] ABSTRACT

A process for the preparation of 2-hydroxy-4-methylthiobutyric acid having improved color, odor and lower viscosity. 2-hydroxy-4-methylthiobutyric acid which is also known as 2-hydroxy-4-(methylthio) butanoic acid, is hydrolyzed with sulfuric acid having an initial strength of between about 50% by weight and about 70% by weight on an organic-free basis, thereby producing an intermediate aqueous hydrolysis product solution containing 2-hydroxy-4-methylthiobutyramide. The 2-hydroxy-4-methylthiobutyramide is hydrolyzed with sulfuric acid having a strength of between about 30% by weight and about 50% by weight on an organic-free basis to produce an aqueous hydrolyzate containing 2-hydroxy-4-methylthiobutyric acid. The hydrolyzate solution is contacted with a substantially water-immiscible organic solvent in a liquid-liquid extraction system to produce an extract comprising the solvent and 2-hydroxy-4-methylthiobutyric acid transferred from the hydrolyzate. The acid product is then recovered from the extract.

24 Claims, 4 Drawing Figures

LIQUID 2-HYDROXY-4-METHYLTHIOBUTYRIC ACID AND PROCESS FOR THE PREPARATION THEREOF

BACKGROUND OF THE INVENTION

This invention relates to the preparation of 2-hydroxy-4-methylthiobutyric acid (HMBA) and more particularly to an improved process for preparing a liquid product comprising HMBA.

2-hydroxy-4-methylthiobutyric acid, commonly referred to as the hydroxy analog of methionine and also known as 2-hydroxy-4-(methylthio)butanoic acid, is an analog of the essential amino acid l-methionine. Methionine analogs such as HMBA are effective in supplying methionine for nutritional uses, particularly as a poultry feed supplement.

Commercially, HMBA has been produced as a racemic D,L-mixture by hydrolyzing 2-hydroxy-4-methylthiobutyronitrile (HMBN) with a mineral acid, precipitating the acid residue by addition of an alkaline earth hydroxide or carbonate, and recovering a salt of HMBA from the aqueous phase by evaporative crystallization. As described, for example, in Blake et al U.S. Pat. No. 2,745,745, either an ammonium salt or mixed ammonium and alkaline earth salts of the acid may be produced, depending on the molar proportions of alkaline earth hydroxide or carbonate added to the hydrolyzate to precipitate the acid residue.

Recently, processes have been developed (e.g., Cummins U.S. Pat. No. 3,773,927) for the preparation of a liquid HMBA product which comprises a high concentration, typically 85% to 90% by weight, HMBA in water. Liquid HMBA products produced in this manner exhibit a strong odor and a relatively dark color. Even when diluted 10:1 in isopropanol, the liquid product usually exhibits readings of 14 or higher on the Gardner Color Scale. Generally, the concentrated liquid product also contains ester oligomers. While most oligomers equilibrate by hydrolysis to monomeric HMBA in a system comprising $\geq 35\%$ by weight water, the rate of such hydrolysis is very slow at 10% to 15% by weight water levels. This results in relatively stable oligomers which impart a relatively high viscosity to the concentrated liquid product.

Discoloration in the liquid product and oligomer formation are believed to result in significant part from exposure of HMBA to conditions of high temperature and low water content during the terminal portion of the dehydration step. Dehydration is also energy-intensive since it is necessary to remove a large proportion of water per unit weight of product. Difficulties are encountered in the filtration or centrifugation steps necessary for separation of by-product solids from the mother liquor. Yields also suffer as a result of the loss of HMBA product adhered to the surfaces of solid by-product salts removed from the process.

As an alternative to evaporative crystallization in the preparation of HMBA salts, Blake (U.S. Pat. No. 2,745,745) contains a limited disclosure of the possibility of separating the acid product from the reaction solution by extraction with a suitable water-immiscible organic liquid which is a solvent for the acid, for example, an organic liquid such as diethyl ether. In one working example, Blake describes a preparation in which HMBN was treated with concentrated hydrochloric acid, the reaction mixture cooled and ammonium chloride allowed to crystallize, the resultant slurry filtered to remove ammonium chloride, and the filtrate extracted with diethyl ether to produce an oily liquid which was treated with saturated zinc acetate solution to produce the zinc salt of HMBA.

British Patent No. 915,193 describes a process for the preparation of the calcium salt of HMBA in which HMBN is hydrolyzed to HMBA in a continuous back-mixed reactor using a dilute sulfuric acid solution, and HMBA is separated from the reaction liquor by extraction with an ether, such as isopropyl ether or butyl ether, which has a boiling point higher than ethyl ether. Water is added to the extract to form an emulsion and calcium carbonate or calcium hydroxide added to the emulsion to precipitate calcium HMBA. The British patent is not concerned with the preparation of a liquid HMBA product. Because of the use of a continuous back-mixed reaction system, the process of the British patent may not achieve complete conversion of HMBN or amide intermediate to HMBA. Although this may not present a problem in the reference process if incompletely reacted material is fully saponified under the alkaline conditions of the salt precipitation, the presence of unreacted material is undesirable where a liquid HMBA product is to be made.

Direct recovery of HMBA from the hydrolyzate by extraction is criticized in Gielkens U.S. Pat. No. 3,175,000 as providing poor yields. Gielken uses extraction for secondary recovery in a process in which HMBA is first salted out of a sulfuric acid hydrolyzate by addition of ammonium sulfate. Residual HMBA in the aqueous phase is thereafter recovered by extraction.

Cummins U.S. Pat. No. 3,773,927 describes a process in which HMBA is produced by hydrochloric acid hydrolysis of HMBN. Under the conditions described by Cummins, the hydrolysis reaction produces a slurry containing solid ammonium chloride which is removed by centrifugation. The filtrate is then vacuum distilled for separation of water. In carrying out the hydrolysis, Cummins expresses a preference for adding the HMBN to a 31% to 38% hydrochloric acid solution at 80° C., after which the mass is heated to 85° C. to 100° C.

SUMMARY OF THE INVENTION

It is an object of the present invention to provide a novel process for the preparation of HMBA and, more particularly, an effective process for the preparation of a concentrated aqueous solution of HMBA having a lighter color, lesser odor, lower viscosity and better thermal stability than the corresponding HMBA product prepared by conventional processes.

It is a further object of the present invention to provide such a process in which HMBA can be produced with relatively low energy cost and overall conversion costs.

It is a still further object of the invention to provide such a process in which a concentrated liquid HMBA product can be produced with a minimum of discoloration or oligomerization in the course of product recovery.

A further object of the invention is the provision of a novel liquid product comprising 2-hydroxy-4-methylthiobutyric acid and exhibiting advantageous properties of color, odor, and viscosity.

Briefly, therefore, the invention is directed to a process for the preparation of 2-hydroxy-4-methylthiobutyric acid (HMBA) in which 2-hydroxy-4-methylthiobutyronitrile (HMBN) is hydrolyzed with a mineral acid to produce an aqueous hydrolyzate containing HMBA and substantially free of unreacted HMBN and intermediate amide. Without separation from the hydrolyzate solution of any substantial fraction of solids that may be present, the hydrolyzate is contacted with a substantially water-immiscible organic solvent in a liquid-liquid extraction system to produce an extract comprising the solvent and HMBA transferred from the hydrolyzate. The conditions of the extraction are controlled so that the extract and an aqueous raffinate are the only liquid phases formed upon phase separation following the extraction. The HMBA is recovered from the extract.

The invention is further directed to a process for the preparation of HMBA in which HMBN is hydrolyzed with a mineral acid to produce an aqueous hydrolyzate containing HMBA. Hydrolyzate solution is contacted with a substantially water-immiscible organic solvent in a liquid-liquid extraction system to produce an extract comprising the solvent and HMBA transferred from the hydrolyzate. The extract is subjected to steam distillation to drive off the solvent and produce a bottom fraction comprising a liquid mixture comprising HMBA and water.

The invention is further directed to a process for the preparation of HMBA in which HMBN is hydrolyzed in a mixture comprising an aqueous mineral acid to produce an aqueous hydrolyzate solution containing HMBA. The aqueous hydrolyzate is contacted with a substantially water-immiscible solvent to produce an extract which comprises the solvent and HMBA transferred from the aqueous solution. The HMBA is separated from the solvent. The solvent has a boiling point of between about 60° C. and about 200° C., the distribution coefficient is at least about 2 for HMBA at equilibrium between the solvent containing the extracted HMBA and the aqueous raffinate remaining after contact between the solvent and the hydrolyzate, and the distribution coefficient is at least about 1.0 between an extract specimen containing HMBA and the aqueous phase remaining after contact between the extract specimen and wash water, and the solubility of water in the solvent is not greater than about 12% by weight at room temperature.

The invention is further directed to a process for preparation of HMBA of improved color and odor, and reduced viscosity. In this process, HMBN is hydrolyzed with sulfuric acid having an initial strength of between about 50% by weight and about 70% by weight on an organic free basis, thereby producing an intermediate aqueous hydrolysis product solution containing 2-hydroxy-4-methylthiobutyramide. The 2-hydroxy-4-methylthiobutyramide is hydrolyzed with sulfuric acid having a strength of between about 30% by weight and about 50% by weight on an organic free basis, thereby producing an aqueous hydrolyzate solution containing HMBA. The hydrolyzate solution is contacted with a substantially water-immisicible organic solvent in a liquid-liquid extraction system to produce an extract comprising the solvent and HMBA transferred from the hydrolyzate. The HMBA is recovered from the extract.

Further included in the invention is a liquid phase animal feed supplement comprising between about 80% and about 95% by weight of the total of the weight proportions of HMBA monomer, dimers, and oligomers, and between about 5% and 20% by weight water. The product has a color of not greater than about 10 as measured on the Gardner scale, a ratio of the weight proportion of HMBA monomer to the weight proportion of the sum of dimers and other oligomers of HMBA of at least about 2.8, and a kinematic viscosity at 25° C., as measured by ASTM method D-445, using a Cannon-Fenske viscometer, of not greater than about 90 centistokes. Upon subjection to differential thermal analysis or accelerating rate calorimetry the product exhibits neither exothermic nor endothermic thermochemical effects at any temperature less than about 150° C.

Other objects and features will be in part inherent and in part pointed out hereinafter.

DESCRIPTION OF THE PREFERRED EMBODIMENTS

The present invention provides a novel and improved process of producing aqueous liquid HMBA products. In a particularly preferred embodiment, the process is adapted to produce an aqueous liquid HMBA solution having a lighter color, lesser odor, lower viscosity and better thermal stability than the corresponding liquid product prepared by conventional processes. Additionally, the process of the invention provides advantages in energy conversion costs in the preparation of HMBA liquid.

Figure 1:
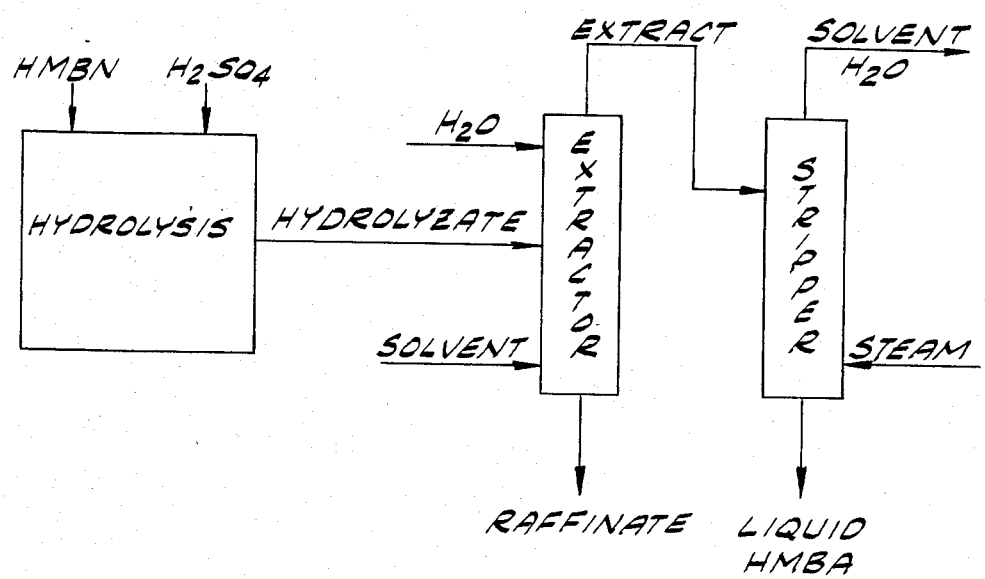
FIG. 1 is a schematic flow sheet illustrating a preferred embodiment of the process of the invention.

Set forth in FIG. 1 is a schematic flow sheet illustrating the steps followed in a particularly preferred embodiment of the process of the invention. In this embodiment, HMBN is first contacted with sulfuric acid and hydrolyzed to provide a light color hydrolyzate containing the HMBA. Thereafter, the hydrolyzate is contacted with a solvent in a liquid-liquid extraction system, thereby transferring the HMBA to an extract comprising the solvent. Extract and raffinate are separated and the extract subjected to steam distillation for removal of solvent. Operation of the steam distillation column is controlled to provide a bottom product comprising the HMBA and water.

Figure 2:
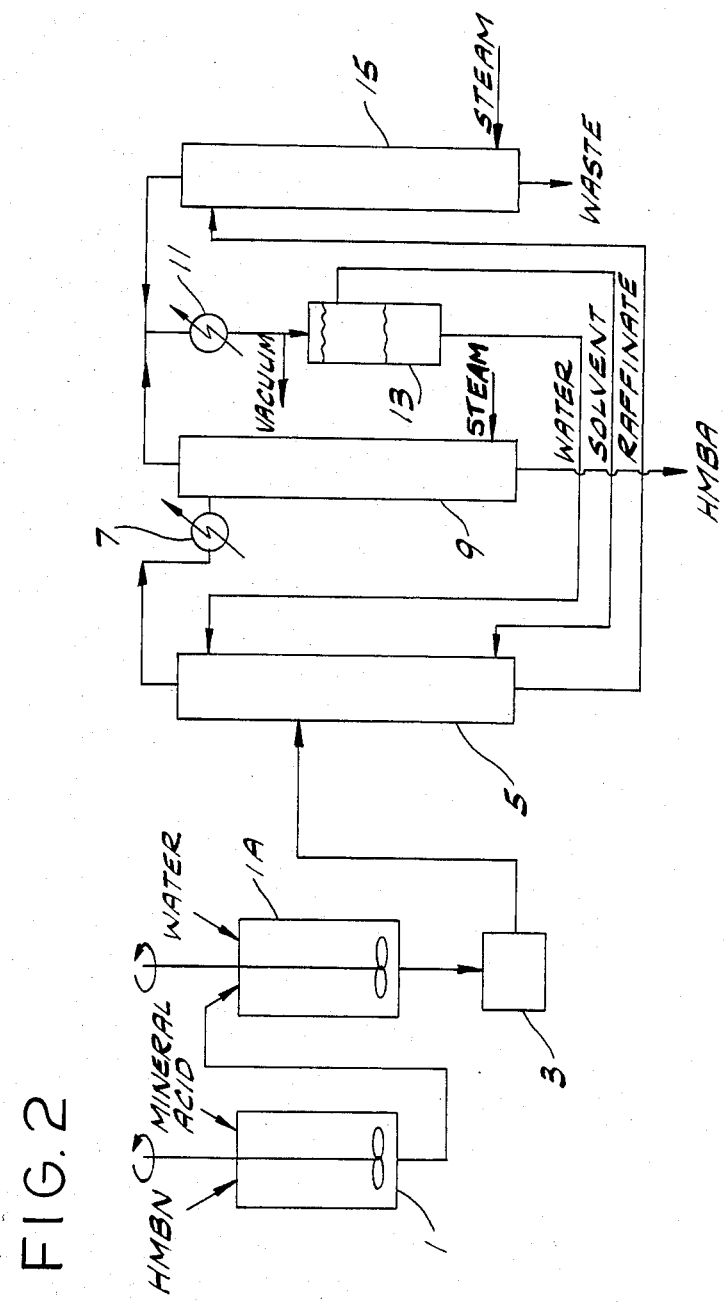
FIG. 2 is a flow sheet for a particular application of the process more generally illustrated in FIG. 1.

After separation from the extract, the aqueous raffinate is also subjected to steam stripping for removal of residual solvent. Solvent overheads from both the extract and raffinate stripping columns are returned to the extraction step, as shown in FIG. 2.

In the hydrolysis step of this preferred process, HMBN is mixed with sulfuric acid having a strength of between about 50% and about 70% by weight, preferably between about 55% and about 65% by weight on an organic free basis at a temperature of between about 25° C. and about 65° C., preferably between about 40° C. and about 60° C. In order to provide effective control of the rate of reaction, the HMBN is preferably added to the acid rather than vice versa. If the acid is added to the nitrile, no reaction takes place until a threshold amount of acid is present, after which the reaction may proceed very rapidly with an exothermic increase in temperature that may detract from the quality of the ultimate product. Typically the addition of nitrile takes place over a period of about 30 to about 60 minutes. Under the preferred conditions, substantial conversion of the nitrile to the amide takes place in a period of between about one-half hour and about one and one-half hours. Thus, the reaction mixture is preferably maintained under agitation in the aforesaid temperature range for about 15 to about 30 minutes after mixing is completed.

Thereafter, 2-hydroxy-4-methylthiobutyramide is converted to HMBA by further hydrolysis at a temperature within the range of between about 70° C. and 120° C., preferably 85° C. to 95° C. Final hydrolysis of the amide to the acid is preferably carried out in sulfuric acid having an initial strength of between about 30% and about 50% by weight, more preferably 30% to 40% by weight, optimally around 40%, on an organic free basis. Where the reaction mixture is heated rapidly to the final hydrolysis temperature, as is preferred for productivity, separation of a separate organic phase generally occurs if the initial acid strength is higher than about 50% by weight on an organic-free basis. To provide the preferred acid strength, it is necessary to dilute the acid phase by adding water before heating the reaction mixture to 70° C. to 120° C. Under conditions of relatively dilute acid strength and increased temperature, the amide is converted to the acid within a period of approximately one and one-half to three hours.

Preferably, sulfuric acid hydrolysis is carried out using approximately one mole of sulfuric acid per mole of the HMBN feed. Generally, an acid excess of 0 to 10%, preferably 0 to 5%, provides satisfactory results.

Although improved product characteristics are obtained where the hydrolysis is carried out with sulfuric acid, a number of the other objects of the invention may still be achieved where the hydrolysis is carried out with another mineral acid such as, for example, hydrochloric acid. Where hydrochloric acid is used, the first hydrolysis step, i.e., conversion of the nitrile to the amide, is preferably initiated by adding HMBN to an acid having a strength of between about 30% and about 40% by weight, preferably 35% to 37% by weight, at a temperature of 25° C. to 60° C., preferably 45° C. to 55° C., over a period of between about 30 minutes and about 60 minutes. As conversion of nitrile to amide progresses, a small amount of solids is normally present. To further hydrolyze the amide to HMBA, the reaction system is rapidly heated to a temperature of between about 70° C. and about 120° C., preferably about 75° C. to about 80° C. Approximately a 15% to 20% excess of HCl is required to complete the hydrolysis of HMBN to HMBA. The final hydrolysis of amide to HMBA is completed in a period of between about 90 minutes and about 180 minutes in a batch reactor.

While the hydrolysis steps of the process can be carried out in either a batch or continuous system, it is important that the hydrolysis reaction be carried substantially to completion. If a continuous reaction system is utilized, it should be designed and operated to assure essentially complete conversion. Thus, for example, continuous operation can be implemented in a plug flow tubular reactor or cascaded stirred tank system. A single back-mixed reactor provides adequate conversion only at residence times that would generally be considered unacceptable for commercial production. Unless very high production volume is needed, a batch reactor is preferred.

After the hydrolysis reaction is complete, irrespective of what acid is used for hydrolysis, volatile impurities are preferably stripped from the hydrolyzate by lowering the pressure over the hot reaction solution to a pressure in the range of between about 50 mm and about 200 mm Hg, and allowing the volatiles and water to distill over until the pot temperature drops to about 55° C. to about 65° C. Where sulfuric acid is used for the hydrolysis, an organic phase separates if too much water is removed in stripping the hydrolyzate. This result is undesirable since it complicates phase relationships and separations in the extraction step. Separation of an organic phase can be avoided by terminating the stripping step at a point which varies with the strength of the sulfuric acid used in the hydrolysis. Thus, for example, where 40% by weight sulfuric acid solution has been used in the hydrolysis step, stripping should generally be terminated before more than about 12% by weight of the hydrolyzate mass has been removed. Stripping of an HCl hydrolyzate should also be terminated before excessive amounts of ammonium chloride salt are precipitated. For either hydrolyzate, stripping is preferably terminated after about 5% to 10% of the mass has been removed.

Before the hydrolyzate solution is introduced into the extraction step, it may also be advantageous to neutralize it and/or to dilute it with water. Neutralization, which is conveniently carried out by addition of anhydrous ammonia to the hydrolyzate, may help to prevent corrosion of process equipment with which the hydrolyzate comes in contact, but may also cause solids formation. Dilution of the hydrolyzate with water causes reabsorption into the aqueous phase of any separate organic phase material, dissolves most or all of any solid salts in the hydrolyzate, and may eliminate solids from the feed to the extraction system. Adequate water content in the hydrolyzate also assures that no solids are formed or accumulate in the extraction system, and no extraneous liquid phases are produced in the extraction. Dilution may be particularly important in the case of hydrochloric acid hydrolysis because of the tendency for significant amounts of NH4Cl to precipitate during the final hydrolysis.

It has been found that, if the strength of the hydrolyzing acid is controlled in the preferred range, dilution of a sulfuric acid hydrolyzate is not generally necessary in order to avoid formation of either solids or extraneous liquid phases. By extraneous liquid phase is meant any phase other than hydrolyzate, solvent, extract and aqueous raffinate, formed prior to or in the extraction of HMBA from the hydrolyzate.

In fact, dilution of the sulfuric acid hydrolyzate to a strength below about 40% by weight (organic-free basis) is preferably avoided so as to capitalize on a particular advantage of sulfuric acid hydrolysis that is associated with the concentration of the ammonium bisulfate/ammonium sulfate by-products of the hydrolysis. Thus, it has been found that the water solubility of the ammonium salt of the acid residue significantly affects the distribution coefficient for HMBA between the extract and raffinate phases. A high salt content tends to salt out HMBA from the aqueous phase and thus improve the distribution coefficient. Based on its high water solubility, therefore, ammonium bisulfate has a particularly beneficial effect on the distribution coefficient. Ammonium bisulfate is superior to ammonium sulfate and ammonium chloride in this regard. In any case, excessive dilution of the hydrolyzate is preferably held to a minimum in order to achieve the most favorable distribution coefficient.

In carrying out the extraction, the solvent utilized should be substantially water-immiscible. However, some mutual solubility between the solvent and water can be tolerated, particularly in the preferred embodiment of the invention where product recovery is accomplished by steam stripping and the aqueous raffinate is also stripped for solvent recovery. It is generally preferred that the solubility of water in the solvent be not greater than about 12% by weight, more preferably not greater than about 8% by weight at room temperature. It is preferred that the solvent have a boiling point of between about 60° C. and about 200° C., more preferably between about 70° C. and about 170° C. The distribution coefficient should be at least about 2 for HMBA at equilibrium between the solvent containing extracted HMBA and the aqueous raffinate remaining after contact between the solvent and the HMBA hydrolyzate. Preferably, this distribution coefficient is at least about 5. Also, the distribution coefficient for HMBA should be at least about 1.0 at equilibrium between an extract specimen and the aqueous phase after contact between such extract specimen and wash water. Additionally, the solvent should be of low toxicity.

A variety of ketones, aldehydes, and alkyl esters of carboxylic acids are particularly suitable as solvents for the extraction. Especially suitable solvents are relatively low molecular weight ketones such as methyl n-propyl ketone, methyl ethyl ketone, methyl amyl ketone, methyl isoamyl ketone, and methyl isobutyl ketone, ethyl butyl ketone, and diisobutyl ketone. Also suitable are aldehydes such as n-butyraldehyde, and esters such as ethyl acetate, n-butyl acetate, n-propyl acetate and isopropyl acetate. Alcohols may also be used but are less desirable because of their high mutual solublity with water, slow phase separation, and tendency to dehydrate, or esterify with, HMBA.

Extraction may be carried out batchwise in a stirred tank, but is preferably conducted in a continuous countercurrent extraction system having an extraction zone which comprises means for promoting mass transfer between the solvent phase and the aqueous phase. Thus, for example, it is advantageous to conduct the extraction in a cascade of continuous countercurrent mixer-settlers, packed column, sieve plate column, rotating disk column, or a centrifugal extractor such as those variously sold under the trade designations "Podbielniak" by Baker-Perkins, "Luwesta" by LUWA, or "DeLaval" by Transamerican DeLaval, Inc. In a particularly preferred embodiment, extraction is conducted in a reciprocating plate column. Intermittent or pulseo flows, though cyclic in terms of instantaneous flow rate, are considered as "continuous" in the context of this disclosure.

The extraction operation is preferably controlled to establish and maintain the solvent phase as the continuous phase in the extraction zone.

To minimize the salt content of the ultimate product, the extract is preferably washed with water. In a continuous countercurrent extraction system, the extract may be washed by mixing water therewith at a location upstream, with respect to the direction of aqueous flow, of the location at which hydrolyzate is introduced into the liquid-liquid extraction system. Thus, for example, in a vertical column using a solvent whose specific gravity is less than 1, solvent is introduced into the column at a location below the feed location at which the aqueous hydrolyzate solution is introduced, and wash water is introouced into the column at a location above the feed point of the hydrolyzate solution. In a preferred embodiment, the solvent is supplied at a rate of about 0.5 parts by weight to 0.6 parts by weight per unit weight of hydrolyzate, thus providing an extract having a specific gravity of about 0.92 to 0.97 and an HMBA content of 35% to 40% by weight.

Productivity of the extraction operation is enhanced by operating at a somewhat elevated temperature in order to provide a relatively low viscosity for the solvent phase within the extraction system. Operation at a temperature in the range of between about 50° C. and about 80° C. also provides a marginally beneficial effect on the HMBA coefficient of distribution between the organic and aqueous phases. Operation in a range of 50° C. to 60° C. further provides a clearer extract than that obtained at 25° C., for example, where slight entrainment may be encountered.

HMBA can be recovered from the extract by distillation, with steam distillation being preferred. By removing the solvent via steam distillation, the bottom product obtained is a liquid mixture of HMBA and water, suitable for direct use as an animal feed supplement. The steam distillation is carried out under conditions such that the bottom fraction is essentially devoid of solvent and contains at least about 5% by weight water, preferably between about 10% and about 15% by weight water and between about 80% and about 95% by weight, preferably 85% to 90% by weight, total HMBA.

Specific column conditions necessarily vary with the particular solvent selected for use in the extraction. Unless the solvent has an exceptionally low boiling point, a plurality of stages is utilized in the stripping column. The steam rate and pressure throughout the column should be controlled to assure that the liquid phase contains between about 4% and about 15% by weight, preferably between about 5% and about 12% by weight, water throughout the column, or at least in the portion of the column below the point of feed introduction. The presence of water helps reduce oligomerization and discoloration in the product. It is further preferred that the liquid phase sojourn time in the column below the feed point be not greater than about one anc one-half hours, preferably not greater than about 45 minutes.

Generally, it is preferred that the temperature at the bottom stage of the column be controlled below 120° C., and a corresponding pressure of not more than about one atmosphere absolute. Whatever the source of hydrolyzate, the pressure at the bottom of the column is preferably maintained in the range of between about 50 mm Hg and atmospheric. However, operation in the upper range of tolerable temperature conditions has been found to provide more favorable vapor/liquid equilibria for separation of the product from a ketone solvent, thus reducing steam requirements.

Although steam distillation is preferred, it is feasible to strip the extract out by distillation using a surface heat transfer reboiler. As a further alternative, stripping may be carried out using a stream of inert gas. Steam distillation, however, is highly preferred because it provides a direct means of producing the liquid product of the invention.

Raffinate may be conveniently subjected to steam distillation or stripping with inert gas for removal of residual solvent. Steam stripping is preferred as a means of solvent recovery from the raffinate.

In accordance with the preferred embodiment of the invention wherein hydrolysis is carried out with sulfuric acid and product is recovered by extraction, and steam distillation stripping, a novel liquid product is produced having highly advantageous properties for use as an animal feed supplement. This product has a total HMBA content, including monomer, dimers, and oligomers, of between about 80% and about 95% by weight, preferably 85% to 90% by weight, and a water content of between about 5% and about 20%, preferably between 10% and about 15% by weight. It has a color of not greater than about 10, and preferably not greater than about 4, as measured undiluted on the Gardner scale per ASTM method D-2849. The ratio of the weight proportion of HMBA monomer to the weight proportion of the sum of dimers and other oligomers thereof is at least about 2.8, preferably at least about 5.7. The kinematic viscosity of the liquid product as measured at 25° C. by ASTM method D-445, using a Cannon-Fenske viscometer, is not greater than abut 90 centistokes, preferably 60 centistokes to 90 centistokes. The amount of odor-causing compounds released from the liquid product at 25° C. to 90° C. is significantly less than the amount released from the corresponding product prepared by conventional processes. Upon subjection to accelerating rate calorimetry this product exhibits neither exothermic nor endothermic thermochemical effects at any temperature less than about 150° C.

Thus, in accordance with the present invention, both an improved process for producing HMBA and an improved aqueous liquid HMBA product are provided. This liquid product is useful as a feed supplement for animals and possesses favorable properties as compared to previous commercially available forms of the hydroxy analog of methionine. If desired, the liquid product may be readily converted to the alkaline earth metal salt of HMBA by precipitation with an alkaline earth metal hydroxide or carbonate. Thus, for example, as described in Cummins U.S. Pat. No. 4,310,690, a lime slurry may be mixed with the liquid product to precipitate calcium HMBA which is recovered from the slurry by centrifugation and dried. Residual calcium HMBA in the mother liquor can be recovered by recycle to the calcium HMBA precipitation step.

In the various embodiments of the present invention oligomerization, discoloration, and degradation of HMBA may be minimized by avoiding exposure of the product to high temperatures for long periods of time in the absence of sufficient proportions of water. Odor causing compounds may be effectively removed from the system in the stripping operation. Since stripping is carried out in a closed system, the odor causing compounds can be contained.

Solids handling is minimized or completely eliminated so that the loss of HMBA product on the surfaces of solid by-products is avoided. Acid strengths and feed ratios in the hydrolysis step are controlled to minimize or eliminate any solids in the hydrolyzate fed to the extraction step. In certain preferred embodiments such as, for example, the use of a reciprocating plate column, the extraction step may be operated so as to tolerate solids in the hydrolyzate feed. Conversion costs in the process of the present invention are reduced by comparison to the previous commercial processes, not only by the elimination of solids separation and solids handling problems, but further because of the substantial reduction in energy requirements for recovering a liquid HMBA product, or evaporative crystallization for producing an HMBA salt. Recovery of organic solvent requires substantially less energy input per unit weight of HMBA product than does dehydration or evaporative crystallization. Elimination of the evaporation and solids separation steps further reduces the capital requirements for implementation of the process of the invention.

Beyond the advantages which are realized through the use of extraction and distillation for recovery of HMBA from the aqueous hydrolyzate, an especially advantageous result is achieved by the combination of sulfuric acid hydrolyzate with liquid-liquid extraction. Surprisingly, where the hydrolysis is carried out with sulfuric acid and the product is recovered by extraction rather than dehydration, the liquid product obtained has a superior color and odor as compared to that produced by either the conventional process or by a combination of hydrochloric acid hydrolysis and extraction. This combination of steps provides the unique liquid product of the invention as described hereinabove.

The following examples illustrate the invention. Unless otherwise specified, all percentages are by weight.

EXAMPLE 1

HMBN (132.10 g., 95% pure by gas chromatography) prepared from methyl mercaptan, acrolein and hydrogen cyanide was added to 50% by weight aqueous sulfuric acid solution (196.14 g) at 50° C. over a 30-minute period in a 1000 ml jacketed flask provided with a stirrer. The resulting mixture was allowed to react for an additional 30 minutes at 50° C. The intermediate hydrolyzate was quickly warmed to 90° C. (within 20 minutes) and reaction continued for an additional 100 minutes at 90° C. After 13 minutes at 90° C., a phase separation occurred in which an organic layer containing HMBA was salted out. After the hydrolysis reaction was complete, a 28% by weight ammonia solution (58.97 g) was added to the hydrolyzate at 80° C. over a 20-minute period. When a little more than half of the ammonia solution had been added, fine crystals began precipitating from the aqueous phase. Near the end point of the ammonia addition, at a pH of 1.76, heavy crystallization made further mixing very difficult.

Three methods were employed for separation of HMBA from the by-products contained in the neutralized hydrolyzate.

In the first of these methods, neutralized hydrolyzate (50 ml; 63 g) was contacted with methyl propyl ketone (50 ml) and water (10 ml) for extraction of the HMBA from the aqueous to the organic ketone phase. Ammonium sulfate crystals remained in the aqueous layer. Both layers were analyzed with the results shown in Table I.

TABLE I

| | HMBA Monomer (%) | HMBA Oligomers (%) | HMBA (%) | H$_2$O (%) |
|---|---|---|---|---|
| Organic layer | 27.7 | 9.03 | 36.7 | 7.53 |
| Aqueous layer | 0.22 | 0.39 | 0.61 | 53.4 |

Solvent was evaporated from the organic layer under vacuum at 70° C. over a 60-minute period, after which the vapor pressure had dropped to 16 mm Hg absolute. The product was analyzed and found to contain 75.5% by weight HMBA monomer, 22.8% by weight HMBA oligomers, and 0.65% by weight water. An 88% by weight solution of the HMBA in water had a Gardner color of 5.

In a second recovery method, neutralized hydrolyzate (50 ml) was contacted with methyl propyl ketone (50 ml) for extraction of HMBA. After contact between hydrolyzate and solvent, phase separation was difficult due to high solids content. After separation was accomplished by overnight settling, both the organic and aqueous layers were analyzed with the results set forth in Table II.

TABLE II

|  | HMBA Monomer (%) | HMBA Oligomers (%) | HMBA (%) | $H_2O$ (%) |
| --- | --- | --- | --- | --- |
| Organic layer | 28.8 | 8.34 | 37.12 | 7.61 |
| Aqueous layer | 0.17 | 0.50 | 0.67 | 52.8 |

After the solvent was evaporated from the organic layer under vacuum at 70° C. over a 60-minute period, at which point the vapor pressure had dropped to 16 mm Hg, the HMBA bottom product was analyzed and found to contain 74.9% by weight HMBA monomer, 23.7% by weight HMBA oligomers, and 0.60% by weight water. Gardner color of an 88% solution of the HMBA product in water was between 4 and 5.

In the third separation scheme, neutralized hydrolyzate was stripped of volatiles under vacuum at 70° C. over a 60-minute period, at which point the vapor pressure had dropped to 15 mm Hg absolute. The slurry produced in the distillation pot was very thick. After filtration for removal of solids, the filtrate was analyzed and found to contain 75.2% by weight HMBA monomer, 20.2% by weight HMBA oligomers, and 3.28% by weight water. An 88% by weight solution of the HMBA product in water exhibited a Gardner color of between 4 and 5.

EXAMPLE 2

HMBN (200 g) prepared in the manner described in Example 1, was slowly added to a 50% by weight sulfuric acid solution (299 g) at 50° C. over a 30-minute period in a 1000 ml jacketed flask. The resulting mixture was allowed to react for an additional 30 minutes. The intermediate hydrolyzate obtained was then quickly warmed to 90° C. (over a 20-minute period) and allowed to react for an additional 100 minutes. After 60 minutes at 90° C., the hydrolyzate acquired a brownish color. The final hydrolyzate comprised two phases.

Without neutralization, the hydrolyzate was contacted with an equal volume of methyl propyl ketone and, after phase separation, solvent was vacuum-distilled from the extract at 70° C. over a 120-minute period. The resulting product comprised 63.6% by weight HMBA monomer, 35.2% by weight HMBA oligomers, 0.11% by weight HMBN, 0.61% by weight of the intermediate amide, 2.11% by weight water, and 0.27% by weight sulfate ions. The Gardner color reading for an aqueous 88% solution of the product was between 5 and 6.

EXAMPLE 3

HMBN (656 g) produced in the manner described in Example 1 was added slowly with stirring to a 50% aqueous sulfuric acid solution (981 g) at 50° C. over a 60-minute period in a 2 liter reactor provided with a propeller stirrer. The resulting solution was allowed to continue reacting for an additional 30 minutes, after which the reaction temperature was increased to 90° C. over a 26 to 30 minute period and held at 90° C. for 120 minutes. After the reaction was over, a portion of the hydrolyzate (1604.4 g) was contacted with methyl propyl ketone (1283.5 g) at 50 to 60° C. in a 5 liter separator flask for about 10 minutes to effect extraction of the HMBA product from the hydrolyzate. Thereafter the aqueous layer was drained from the flask and the extract layer (2073.2 g) was washed with water (207.5 g) at 50° C. The aqueous layer (48.8 g; 6.0% HMBA) was drained from the flask.

Solvent was evaporated from the extract under vacuum at 50° C. with the distillation continued until the vapor pressure had dropped to 30 mm Hg. At that point water (20 ml) was added subsurface to the residue in the distillation pot and the temperature increased to 70° C. for steam distillation of the residual solvent. When the vapor pressure had dropped to 20 mm Hg absolute at 70° C., steam distillation was terminated. The neat product in the distillation pot following steam distillation was analyzed and found to contain 74.0% by weight HMBA monomer, 24.4% by weight HMBA oligomers, 1.8% by weight water and 0.45% by weight sulfate ions. Dilution of this product to 88% by weight HMBA by addition of water produced a product which exhibited a Gardner color between 5 and 6.

EXAMPLE 4

HMBN (263.16 g) prepared in the manner described in Example 1 was added slowly to a 65% by weight sulfuric acid solution (301.45 g) at 50° C. over a 60 minute period in a 1000 ml jacketed flask provided with a stirrer. The resulting mixture was allowed to continue reacting for an additional 30 minutes at 50° C. Water (188.91 g) was then added to the intermediate hydrolyzate to dilute the strength of the hydrolyzing acid. The temperature of the contents of the reactor was then increased from 50 to 90° C. (over a 25 minute period) and held at 90° C. for 115 minutes.

During the first stage of the hydrolysis (i.e., reaction in 65% by weight initial strength sulfuric acid solution at 50° C.) the viscosity of the reaction mixture was observed to increase significantly so that the reaction system tended to form two distinct phases, one containing the intermediate 2-hydroxy-4-methylthiobutyramide and the other containing HMBN freshly added to the mixture. Throughout the second stage of the hydrolysis, i.e. conversion, of the intermediate amide to the acid product at 90° C., a single phase was maintained without any phase separation. At the end of the hydrolysis, the hydrolyzate was analyzed and found to contain 35.2% by weight HMBA monomer, 0.31% by weight HMBA dimer, 0.01% by weight HMBN and 0.01% by weight amide intermediate.

Figure 4:
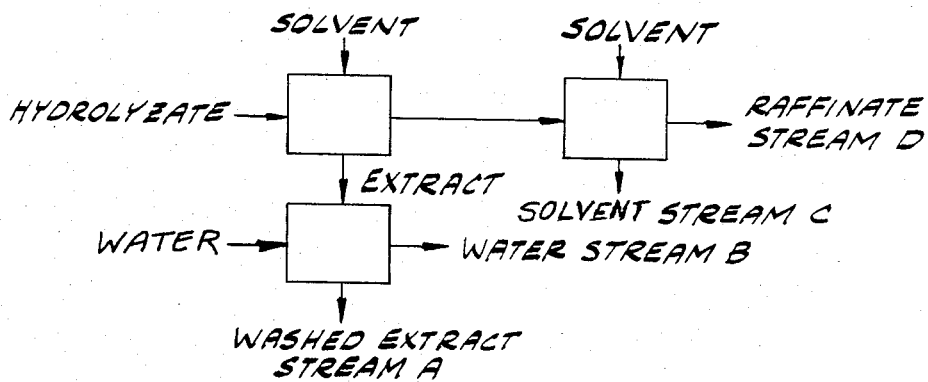
FIG. 4 is a schematic illustration of an extraction system used in the measurement of distribution coefficients.

Another portion of the HMBA hydrolyzate of this example was subjected to extraction using a variety of solvents. Extraction was carried out using the scheme illustrated in FIG. 4.

In each instance 100 parts by weight hydrolyzate was contacted with 60 parts by weight solvent in a separatory flask. After mixing and separation of phases, 100 parts by weight of the organic layer was washed with 12.5 parts by weight of water and the aqueous raffinate (100 parts by weight) was washed with 60 parts by weight of the solvent. All extractions were made at room temperature, i.e. 25° C. Distribution coefficients were determined for each solvent at equilibrium between the organic and aqueous phases. The distribution coefficient was defined as the ratio of the concentration of HMBA in the organic phase to the concentration of HMBA in the aqueous phase. The results of the extraction runs of this example are set forth in Table III.

TABLE III

| Solvent (boiling point) | Distribution Coefficients | |
|---|---|---|
| | Extract vs. Wash Water | Solvent vs. Raffinate |
| Methyl ethyl ketone (79.6° C.) | 5.4 | 14.6 |
| Methyl n-propyl ketone (102° C.) | 4.3 | 6.2 |
| Methyl isobutyl ketone (116.9° C.) | 2.6 | 4.7 |
| n-Butanol (117.3° C.) | 15.4 | 24.0 |
| iso-Butanol (107.9° C.) | 11.2 | 9.7 |
| sec-Butanol (99.5° C.) | 9.6 | 11.9 |
| tert-Butanol (82.8° C.) | no phase separation | 20.5 |
| 2-Pentanol (118.9° C.) | 5.2 | 15.3 |
| n-Amyl alcohol (137.5° C.) | 12.3 | 15.3 |
| n-Butyraldehyde (75.7° C.) | 1.4 | 12.6 |
| Ethyl acetate (77.1° C.) | no phase separation | 6.3 |
| n-Butyl acetate (126.5° C.) | 1.9 | 4.9 |
| n-Propyl acetate (101.6° C.) | 2.4 | 7.5 |
| iso-Propyl acetate (90° C.) | 2.3 | 5.4 |
| Diethyl ether (34.6° C.) | 2.6 | 4.5 |
| di-Isopropyl ether (68° C.) | <0.1 | 2.1 |
| Methylene chloride (40° C.) | 6.7 | 0.6 |
| Dichloroethane (83.5° C.) | 10.4 | 0.8 |
| Trichloroethylene (86.7° C.) | 9.2 | 1.8 |

EXAMPLE 5

HMBA was prepared using the process scheme illustrated in FIG. 2. In this system, HMBA hydrolyzate is prepared in a batch reaction system comprised of a single stirred tank reactor but in two reaction stages represented schematically as 1 and 1A. HMBN is added slowly to sulfuric acid in stage 1 where HMBN reacts in the acid to produce an intermediate hydrolyzate containing 2-hydroxy-4-methylthiobutyramide. The intermediate hydrolyzate is diluted by addition of water and the temperature increased for conversion of the intermediate amide to HMBA (reactor stage 1A). Final hydrolyzate from reactor stage 1A is dumped into a surge drum 3. From there it is fed continuously to approximately the center point of a Karr reciprocating plate extraction column 5 to which solvent is fed near the bottom and wash water near the top. Overhead extract is preheated in a heat exchanger 7 and fed to a steam distillation column 9. Bottoms from column 9 comprise a liquid product containing HMBA and water. Overhead vapors from column 9 are condensed in the condenser 11 and delivered to a separator 13 from which solvent is recycled to the bottom of extraction column 5 and water is recycled to the top of the extraction column for washing.

Raffinate exiting the bottom of extraction column 5 is subjected to steam stripping in column 15 for recovery of residual solvent in the overhead vapors which are also directed to condenser 11 where they are condensed and delivered to separator 13. The bottoms from column 15 constitute aqueous waste and are discarded.

For a typical hydrolysis batch in the operation of this example, 65.1% by weight sulfuric acid (142.3 kg) was charged to reactor stage 1 and HMBN (120.1 kg) added slowly to the reactor over a period of 61 minutes at a temperature of 50° C. to 54° C. In stage 1A, intermediate hydrolyzate was diluted to 40.1% acid strength (on an organic-free basis) by addition of water and heated to 89° C. over a period of 30 minutes. The hydrolyzate was then held at 90° C. for an additional 75 minutes. Volatile components were then removed by gradually reducing the pressure to about 110 mm Hg absolute over about a 45 minute period while letting the temperature drop to about 65° C. About 11 kg of material was boiled off. The hydrolyzate was then discharged into surge drum 3.

Final hydrolyzate from drum 3 was fed continuously to column 5 at a rate of 181 g/min and methyl isobutyl ketone (MIBK) solvent fed to the bottom of the extraction column at 100 g/min. Wash water was charged to the top of the column. Continuous counter-current extraction was conducted in column 5 at a temperature of about 59° C. and a plate reciprocation rate of 140 to 228 strokes per minute, producing an extract which was discharged from the top of the column and an aqueous raffinate which was discharged from the bottom of the column. Extract preheated in exchanger 7 was delivered to steam stripping column 9 where solvent was stripped at a 235 mm Hg column head pressure, and at a temperature of 82° C. at the top of the column and 88° C. at the bottom of the column to produce 78 g/min bottoms product comprising an aqueous solution of HMBA. The overhead vapors comprised 100 g/min MIBK and 50 g/min water which were condensed in condenser 11 and delivered to separator 13. Raffinate from the bottom of column 5 was steam stripped in column 15 at a column head pressure of 760 mm Hg, a head temperature of 97° C. and a pot temperature of 107° C., producing an overhead vapor stream containing 0.9 g/min MIBK and 5 g/min water which were mixed with the overhead vapors from column 9, condensed in condenser 11 and delivered to separator 13. Bottoms from raffinate stripping column 15 were produced at a rate of 144 g/min and passed to waste disposal.

Extraction column 5 was a 2.54 cm dia×2.1 m high Karr reciprocating plate column.

After steady-state operation was achieved, both the hydrolyzate leaving drum 3, and the aqueous product discharged from the bottom of extract stripping column 9 were sampled periodically for analysis. The range of results obtained by these analyses are set forth in Table IV.

TABLE IV

| | Hydrolyzate % | Product % |
|---|---|---|
| HMBA | 38.2~42.3 | 89.2~91.8 |
| Water | 25.1~28.4 | 8.20~10.8 |
| Sulfate ion | 25.6~28.0 | 0.45~1.3 |
| HMBA monomer | 33.9~35.1 | 72.8~80.2 |
| HMBA oligomers | 4.3~7.2 | 11.4~16.9 |
| Color (Gardner) | 2~4 | 3.5~5.5 |

EXAMPLE 6

Hydrolyzate was prepared in the manner of Example 5. Feed of the hydrolyzate to the Karr reciprocating plate extractor column was 204 g/min. The column was operated at 60° C. with a MIBK solvent input rate of 112 g/min and a wash water input rate of 23 g/min, and a plate reciprocation rate of 170 strokes per minute, producing an extract which was preheated to a temperature of 99.5° C. at a pressure of 451 mm Hg absolute and delivered to the extract stripper. The stripper was operated at a head pressure of 451 mm Hg, a head temperature of 99.5° C. and a pot temperature of 102° C. to produce a concentrated HMBA aqueous liquid product at 94.0 g/min at the bottom of the column. Overhead vapors from the extract stripper were produced at a rate of 112 g/min MIBK and 42.5 g/min water. These vapors were mixed with overhead vapors from the raffinate stripper, condensed and delivered to the separator. Raffinate produced at the bottom of the extraction column was delivered to the raffinate stripper where solvent was removed by stripping at a head pressure of 451 mm Hg, a head temperature of 93° C., and a bottom temperature of 94° C. Overhead vapors were produced at a rate of 0.7 g/min MIBK and 12.5 g/min water. These vapors were mixed with overhead vapors from the extract stripper, condensed and delivered to the separator. Bottoms from the raffinate stripper comprised aqueous waste which was produced at a rate of 129.0 g/min and discarded.

When steady state was achieved in the operation of this example, samples of hydrolyzate and product were taken periodically and analyzed. Set forth in Table V are the results of these analyses.

TABLE V

|  | Hydrolyzate % | Product % |
|---|---|---|
| HMBA | 41.2~41.6 | 87.1~91.9 |
| Water | 25.5~26.6 | 11.8~12.2 |
| Sulfate ion | 27.1~27.9 | 0.52~0.62 |
| HMBA monomer | — | 74.9~75.4 |
| HMBA oligomers | — | 13.8~15.0 |
| Color (Gardner) | — | 3 |

EXAMPLE 7

A 63.1% by weight sulfuric acid solution (1555 g containing 980 g, i.e. 10 moles, sulfuric acid) was introduced into a 5 L stirred reactor. Over a period of one hour, HMBN (1310 g; 10 moles) was added to the sulfuric acid in the reactor at a temperature of 50° C. while the reactor was cooled by means of an ice bath. After addition of the nitrile was complete, the resultant mixture was maintained at a temperature of 50° C. for one-half hour.

After the mixture was held at 50° C. for one-half hour, water (900 g) was added, and the resultant diluted mixture was heated to 90° C. over a period of one hour and held for an additional hour for conversion of the amide to the product acid.

The final hydrolyzate was evaporated under vacuum at 70 to 90° C. until a terminal pressure of 100 mm Hg was reached, which resulted in removal of 37 g of volatiles. A minor amount of solids precipitated in the course of the stripping of volatiles from the hydrolyzate and 2.2 g of water were added to dissolve the solids.

Figure 3:
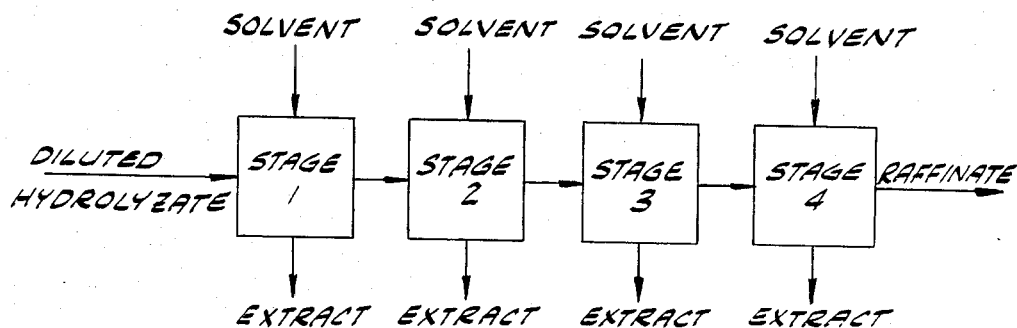
FIG. 3 is a schematic illustration of a crossflow extraction system which may be utilized in the process of the invention.

HMBA was recovered from a portion of the hydrolyzate using a four-stage cross flow extraction system of the type illustrated in FIG. 3. In the extraction operation of this example, hydrolyzate (200 g) and MIBK (40 g) were mixed in the first stage, producing an extract and a raffinate. A portion (100 g) of the raffinate was delivered along with additional MIBK (20 g) to the second stage. After separation of the second stage extract, 85 g of raffinate from the second stage was transferred to the third stage where it was mixed with a further portion MIBK (17 g). After separation of extract in the third stage, 70 g of raffinate from the third stage was mixed with MIBK (14 g) in the fourth stage. The extractions were all carried out at room temperature. After separation of phases in each stage of the extraction, both extract and raffinate stages were analyzed for HMBA with the results set forth in Table VI.

TABLE VI

| Stage | HMBA Analyses (% by weight) | |
|---|---|---|
| | Extract | Raffinate |
| 1 | 57.6 | 5.67 |
| 2 | 16.4 | 1.82 |
| 3 | 5.5 | 0.70 |
| 4 | 2.0 | 0.28 |

EXAMPLE 8

HMBN (18.16 kg) was added to a 34.7% by weight solution of hydrochloric acid (16.72 kg) in a 380 liter glass-lined reactor with jacket cooling. The temperature of the resulting mixture increased from 30° C. to 50° C. over a 15 minute period, and was maintained between 50° C. and 60° C. over a two hour period to produce an intermediate hydrolyzate containing 2-hydroxy-4-methylthiobutyramide. Thereafter the temperature was increased to 82° C. over a 15 minute period and held at approximately 80° C. for 90 minutes to produce a final hydrolyzate containing HMBA.

This hydrolyzate (34.89 kg) was partially neutralized by adding thereto a 29.5% ammonium hydroxide solution (0.84 kg), and the neutralized hydrolyzate was partially distilled under a vacuum at 70° C. for removal of volatile impurities. Prior to distillation, wash water from another operation and containing HMBA was mixed with neutralized hydrolyzate. Initial head pressure in the distillation was 150 mm Hg absolute and the pressure fell to 25 mm Hg absolute over a period of 160 minutes at 70° C. As distillation progressed sufficient water was stripped off so that ammonium chloride salt precipitated, forming a slurry in the distillation pot.

This slurry (100 parts by weight) was diluted with water (64 parts by weight) to dissolve the ammonium chloride salt in the aqueous phase. Portions (20.0 g each) of the stripped and diluted hydrolyzate were mixed vigorously for about 15 minutes at room temperature with each of the solvents listed below. After mixing, the phases were separated and analyzed for HMBA. Set forth in Table VII are the results of these analyses and the distribution coefficients calculated for the single stage extractions of this example.

TABLE VII

| Solvent | HMBA ANALYSES (% By Weight) | | Distribution Coefficient |
|---|---|---|---|
| | Extract | Raffinate | |
| 1-butanol | 22.8% | 3.2% | 7.1 |
| 1-pentanol | 23.8% | 3.9% | 6.1 |
| 2-pentanol | 23.0% | 4.9% | 4.7 |
| methyl ethyl ketone | 22.3% | 4.9% | 4.6 |
| methyl isobutyl ketone | 21.0% | 8.4% | 2.5 |
| ethyl acetate | 23.7% | 10.6% | 2.2 |
| n-propyl acetate | 20.8% | 10.2% | 2.0 |
| ethyl ether | 24.7% | 8.2% | 3.0 |
| methyl n-propyl ketone | 21.4% | 6.0 | 3.6 |

EXAMPLE 9

A portion of the hydrolyzate slurry of Example 8 (100 parts by weight) was diluted with water (40 parts by weight) at 70° C. to dissolve the solid ammonium chloride salt contained therein. A portion (20.0 g) of the diluted hydrolyzate was mixed vigorously with MIBK (20.0 g) for fifteen minutes at 70° C. The phases were separated and analyzed for HMBA.

This work up and extraction was repeated for 1-butanol.

Results of analyses of the extracts and raffinates produced in this example are set forth in Table VIII, together with the distribution coefficients calculated from the analytical data.

TABLE VIII

| Solvent | HMBA ANALYSES (% By Weight) | | Distribution Coefficient |
| --- | --- | --- | --- |
| | Extract | Raffinate | |
| 1-butanol | 26.8% | 8.9% | 3.0 |
| methyl isobutyl ketone | 23.8% | 10.0% | 2.4 |

EXAMPLE 10

A portion of the HCl hydrolyzate slurry (100 parts by weight) produced in Example 8 was diluted with water (64 parts by weight) to dissolve ammonium chloride solids. This diluted hydrolyzate was then subjected to a four-stage cross-flow extraction, using a system of the type illustrated in FIG. 3. In this extraction operation, hydrolyzate (200 g) and methyl n-propyl ketone (100 g) were mixed in the first stage and allowed to separate into an extract and a raffinate. A portion of the first stage raffinate (110 g) was delivered along with additional methyl n-propyl ketone (55 g) to the second stage. After phase separation in the second stage, a portion of the second stage raffinate (88 g) was transferred to the third stage, where it was mixed with a further portion of methyl n-propyl ketone (44 g). After separation of the extract from the third stage, a portion of the third stage raffinate (71 g) was mixed with additional methyl n-propyl ketone (35.5 g) in the fourth stage. The extractions were all carried out at room temperature. After separation of phases in each stage of the extraction, both extract and raffinate stages were analyzed for HMBA with the results set forth in Table IX.

TABLE IX

| Stage | HMBA Analyses (% by weight) | |
| --- | --- | --- |
| | Extract | Raffinate |
| 1 | 32.1% | 9.1% |
| 2 | 10.1% | 4.5% |
| 3 | 3.1% | 1.7% |
| 4 | 1.4% | 1.0% |

The extract from stage 1 of the extraction operation of this example contained 0.89% ammonium chloride. A portion of this extract (80.0 g) was mixed vigorously with water (4.0 g) for about fifteen minutes. The phases were then separated and the washed extract was again analyzed for ammonium chloride. The ammonium chloride content had been reduced to 0.51%.

EXAMPLE 11

Water was added to an HCl hydrolyzate taken from a commercial plant for the manufacture of HMBA. By the addition of water, ammonium chloride solids in the hydrolyzate were dissolved, and a diluted hydrolyzate was produced containing 38.2% by weight HMBA and 15.3% by weight ammonium chloride. This hydrolyzate was fed at a rate of 166 g/min to the top of a 2.54 cm diameter reciprocating plate extraction column having a 162.6 cm high plate stack. Methyl n-propyl ketone was fed to the bottom of the column at a rate of 99 g/min. The solvent phase was continuous throughout the extraction zone. Samples of the extract and raffinate showed that the HMBA content of the extract was 35.4% and the HMBA content of the raffinate was 0.36% by weight.

EXAMPLE 12

A sample of an HCl hydrolyzate produced in a commercial HMBA manufacturing plant was subjected to extraction without prior dilution to dissolve ammonium chloride solids suspended in the hydrolyzate. The hydrolyzate slurry, containing 61.8% by weight HMBA and 23.6% by weight ammonium chloride (total dissolved and suspended), was fed from an agitated vessel to a 2.54 cm diameter reciprocating plate extraction column at a rate of 125 g/min at a point 30.5 cm below the top of the plate stack. Water was fed to the top of the column at a rate of 22 g/min. MIBK solvent was fed to the bottom of the plate stack (total height: 162.6 cm) at a rate of 98 g/min. The MIBK was the continuous phase throughout the extraction zone. Operating temperature of the extraction was 50° C. The extract was analyzed and found to contain 41.1% HMBA and 0.36% ammonium chloride. The raffinate contained 0.57% HMBA and a large volume of ammonium chloride crystals.

This example demonstrates that the preferred embodiment of the extraction step can be conducted without prior separation of solids, even in the case where the hydrolyzate feed and raffinate contain substantial volumes of salt crystals. Based on the results of this and similar runs, it has been found that the solids are essentially contained within the aqueous phase and that an essentially solid-free extract is produced.

EXAMPLE 13

HMBN (107.6 kg) was added to a 64.9% by weight solution of sulfuric acid (123.9 kg) in a 38 liter glass lined reactor provided with an external heat exchanger, circulating pump and associated piping for circulation and cooling of the reactor contents. Addition of the nitrile took place over a 59 minute period. During the first nine minutes, the mixture warmed from 30° C. to 60° C., and during the last 50 minutes the temperature was maintained at 60° C. After addition of the nitrile was complete, the mixture was stirred for an additional 15 minutes at 60° C., thus producing an intermediate hydrolyzate.

Thereafter, water (77.2 kg) was added to the reaction mixture and the mixture heated from 60° C. to 89° C. over a 30 minute period. The mixture was then held at 89° C. for an additional 88 minutes to produce a final hydrolyzate containg HMBA.

When the hydrolysis was complete, the contents of the reactor were placed under vacuum and 21 lbs (9.5 kg) of water and volatiles were boiled off.

After stripping of volatiles the hydrolyzate was fed at a rate of 204 g/min to a 2.54 cm diameter reciprocating plate extraction column at a point 61 cm below the top of the 244 cm plate stack. Water (23.5 g/min) was fed to the top of the column and MIBK (112 g/min) was fed to the bottom. MIBK was the continuous phase in the extraction zone. The extraction column was operated at a temperature of about 60° C. Extract from the top of the column was passed through a pre-heater where it was heated to 115° C. at atmospheric pressure. A substantial proportion of the MIBK boiled off under those conditions. The remaining organic liquid phase was fed to the top of a stripping column, 7.6 cm dia×229 cm high, packed with Cannon 0.64 cm protruded metal packing. Steam was fed to the bottom of the column at a rate of 19 g/min. The pressure at the top of the column was maintained at atmospheric and the temperature at the bottom of the column was 116° C. The bottom product was analyzed and found to contain 88.9% HMBA, 0.56% sulfate ion, and the balance water. Gardner color of the product was 4.

EXAMPLE 14

An HMBA hydrolyzate was prepared in the manner generally described in Example 13.

This hydrolyzate was extracted by feeding it at a rate of 201 g/min through a 2.54 cm diameter reciprocating plate extraction column at a point 61 cm below the top of the 244 cm stack. Water was fed into the top of the column at a rate of 22.5 g/m and MIBK was fed into the bottom of the column at a rate of 111 g/min. The solvent phase was maintained as the continuous phase in the extraction zone. The column operated at a temperature of about 60° C.

Extract from the top of the reciprocating plate column was passed through a heat exchanger where it was heated to 71° C. at a pressure of 147 mm of Hg. A substantial fraction of the MIBK was boiled off under these conditions and the remaining liquid phase was fed to the top of a stripping column of the type described in Example 13. Steam at a rate of 28.5 g/min was fed into the bottom of the column. Column head pressure was 147 mm Hg. A bottom product was obtained which was analyzed and found to contain 89.0% by weight HMBA, 0.54% by weight sulfate ion, and the balance essentially water.

In view of the above, it will be seen that the several objects of the invention are achieved and other advantageous results attained.

As various changes could be made in the above processes and methods without departing from the scope of the invention, it is intended that all matter contained in the above description or shown in the accompanying drawings shall be interpreted as illustrative and not in a limiting sense.

What is claimed is:

1. A process for the preparation of 2-hydroxy-4-methylthiobutyric acid having improved color, odor and lower viscosity, comprising the steps of
    hydrolyzing 2-hydroxy-4-methylthiobutyronitrile with sulfuric acid having an initial strength of between about 50% by weight and about 70% by weight on an organic-free basis, thereby producing an intermediate aqueous hydrolysis product solution containing 2-hydroxy-4-methylthiobutyramide;
    hydrolyzing said 2-hydroxy-4-methylthiobutyramide with sulfuric acid having a strength of between about 30% by weight and about 50% by weight on an organic-free basis, thereby producing an aqueous hydrolyzate solution containing 2-hydroxy-4-methylthiobutyric acid;
    contacting said hydrolyzate solution with a substantially water-immiscible organic solvent in a liquid/liquid extraction system to produce an extract comprising said solvent and 2-hydroxy-4-methylthiobutyric acid transferred from said hydrolyzate; and
    recovering said 2-hydroxy-4-methylthiobutyric acid from said extract in the presence of about 5% or more by weight water based on the amount of recovered 2-hydroxy-4-methylthiobutyric acid.

2. A process as set forth in claim 1 wherein the hydrolysis reactions are conducted under conditions which provide for substantially complete conversion so that said hydrolyzate is substantially free of residual 2-hydroxy-4-methyl-thiobutyronitrile and 2-hydroxy-4-methylthiobutyramide.

3. A process as set forth in claim 1 wherein the hydrolysis reactions are conducted batchwise, said 2-hydroxy-4-methylthiobutyronitrile being added to a vessel containing sulfuric acid while agitating the contents of the vessel.

4. A process as set forth in claim 3 wherein said 2-hydroxy-4-methylthiobutyronitrile is added to sulfuric acid and hydrolyzed at a temperature of between about 25° C. and about 65° C. to produce said intermediate aqueous hydrolysis product solution containing 2-hydroxy-4-methylthiobutyramide; and
    said 2-hydroxy-4-methylthiobutyramide is hydrolyzed at a temperature of between about 70° C. and about 120° C. to produce said hydrolyzate solution.

5. A process as set forth in claim 4 wherein said 2-hydroxy-4-methylthiobutyronitrile is added to sulfuric acid having an initial strength of between about 55% and about 65% by weight and 2-hydroxy-4-methylthiobutyronitrile is hydrolyzed to 2-hydroxy-4-methylthiobutyramide at a temperature of between 40° C. and about 60° C.; and
    said 2-hydroxy-4-methylthiobutyramide is hydrolyzed 2-hydroxy-4-methylthiobutric by reaction with sulfuric acid having a strength of between about 30% and about 40% by weight on an organic free basis at a temperature of between about 85° C. and about 95° C.

6. A process as set forth in claim 1 wherein said 2-hydroxy-4-methylthiobutyric acid is transferred from said aqueous hydrolyzate to said solvent by continuous countercurrent extraction.

7. A process as set forth in claim 6 wherein the extraction is carried out in a countercurrent extraction system in which said extract is washed by mixing water therewith at a location upstream, with respect to the direction of aqueous flow, of the location at which hydrolyzate is introduced into said system.

8. A process as set forth in claim 6 wherein the extraction is carried out in a continuous countercurrent extraction system having an extraction zone comprising means for promoting mass transfer between the solvent phase and the aqueous phase therein, and the extraction operation is controlled to establish and maintain the solvent phase as the continuous phase in said extraction zone.

9. A process as set forth in claim 1 wherein said solvent has a boiling point of between about 60° C. and about 200° C., the distribution coefficient is about 2 or more for 2-hydroxy-4-methylthiobutyric acid at equilibrium between said solvent containing 2-hydroxy-4-methylthiobutyric acid and an aqueous raffinate remaining after contact between said solvent and said hydrolyzate, the distribution coefficient is about 1.0 or more at equilibrium between an extract specimen containing 2-hydroxy-4-methylthiobutyric acid and the aqueous phase after contact between said extract specimen and wash water, and the solubility of water in said solvent at room temperature is not higher than about 12% by weight.

10. A process as set forth in claim 9 wherein said boiling point is between about 70° C. and about 170° C., and said solubility is not greater than about 8% by weight.

11. A process as set forth in claim 9 wherein said solvent is selected from the group consisting of ketones, aldehydes, and alkyl esters of carboxylic acids.

12. A process as set forth in claim 1 wherein said solvent is selected from the group consisting of methyl propyl ketone, methyl ethyl ketone, methyl isobutyl ketone, methyl amyl ketone, ethyl butyl ketone diisobutyl ketone, and methyl isoamyl ketone.

13. A process as set forth in claim 1 wherein the hydrolyzate is subjected to extraction without prior separation from said hydrolyzate of any substantial fraction of any solids present therein, and the water content of the raffinate is sufficient that solids do not accumulate in the extraction system.

14. A process as set forth in claim 13 wherein the water content of the hydrolyzate as introduced into the extraction system is sufficient so that no substantial proportions of solids are introduced into said system.

15. A process as set forth in claim 14 wherein the water content of the hydrolyzate as introduced into said system is sufficient that no substantial proportion of solids is formed in said system.

16. A process as set forth in claim 14 wherein the water content of said mixture is sufficient to prevent solids from forming as a result of the hydrolysis.

17. A process as set forth in claim 1 wherein prior to extraction said hydrolyzate is partially distilled under reduced pressure.

18. A process as set forth in claim 17 wherein said distillation is terminated prior to the separation of an organic liquid phase from the hydrolyzate.

19. A process as set forth in claim 17 wherein the hydrolyzate is diluted with water after the distillation to effect reabsorption of any organic phase material separated from the hydrolyzate.

20. A process as set forth in claim 1 wherein said extract is subjected to steam distillation to drive off said solvent and produce a bottom fraction comprising a liquid product comprising 2-hydroxy-4-methylthiobutyric acid and water.

21. A process as set forth in claim 20 wherein said distillation is conducted in a column containing a plurality of equilibrium stages and the bottom stage thereof is controlled at a temperature not higher than about 120° C. and a pressure not higher than about one atmosphere absolute.

22. A process as set forth in claim 20 wherein the residence time of 2-hydroxy-4-methylthiobutyric acid in the distillation column is not greater than about one and one-half hours.

23. A process as set forth in claim 21 wherein the steam distillation operation is controlled to maintain about 4% or more by weight water in the liquid phase throughout the distillation column.

24. A liquid phase animal feed supplement comprising between about 80% and about 95% by weight of the total of weight proportions of 2-hydroxy-4-methylthiobutyric acid monomer, dimers, and oligomers, and between about 5% and about 20% by weight water, and having a color of not greater than about 10 as measured on the Gardner scale, a ratio of the weight proportions of monomer to the weight proportions of the sum of dimers and other oligomers of about 2.8 or more, a kinematic viscosity at 25° C. as measured by a Cannon-Fenske viscometer of not greater than about 90 centistokes, and which, upon subjection to accelerating rate calorimetry exhibits neither exothermic nor endothermic thermochemical effects at any temperature less than about 150° C.

* * * * *

UNITED STATES PATENT AND TRADEMARK OFFICE
CERTIFICATE OF CORRECTION

PATENT NO. : 4,524,077
DATED : June 18, 1985
INVENTOR(S) : Dennis A. Ruest et al It is certified that error appears in the above-identified patent and that said Letters Patent is hereby corrected as shown below:

Claim 1, line 2 ,"odor" should be deleted.

Claim 1, lines 24-26 should read "from said extract by removal of the organic solvent in the presence of about 5% or more by weight based on the remaining extract."

Claim 5, lines 8-9 between "is" and "by" should read --hydrolyzed to 2-hydroxy-4-methylthiobutyric acid--.

Signed and Sealed this

Twenty-fifth Day of March 1986

[SEAL]

Attest:

DONALD J. QUIGG

Attesting Officer

Commissioner of Patents and Trademarks